US011224530B2

(12) United States Patent
Halbert et al.

(10) Patent No.: US 11,224,530 B2
(45) Date of Patent: Jan. 18, 2022

(54) STENT DELIVERY CATHETER WITH FAST SLIDER AND SLOW THUMBWHEEL CONTROL

(71) Applicant: Cardinal Health Switzerland 515 GmbH, Baar (CH)

(72) Inventors: Phillip Halbert, Milpitas, CA (US); Matt Gill, Milpitas, CA (US); Sean Higginson, Milpitas, CA (US)

(73) Assignee: Cardinal Health Switzerland 515 GmbH, Baar (CH)

( * ) Notice: Subject to any disclaimer, the term of this patent is extended or adjusted under 35 U.S.C. 154(b) by 206 days.

(21) Appl. No.: 16/128,160

(22) Filed: Sep. 11, 2018

(65) Prior Publication Data
US 2019/0076279 A1 Mar. 14, 2019

Related U.S. Application Data

(60) Provisional application No. 62/557,923, filed on Sep. 13, 2017.

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05)

(58) Field of Classification Search
CPC ................ A61F 2/9517; A61F 2/966; A61F 2/962–9662; A61F 2/954; A61F 2002/9623–9665; A61F 2002/9534
See application file for complete search history.

(56) References Cited

U.S. PATENT DOCUMENTS

| 4,580,568 | A | 4/1986 | Gianturco |
| 4,732,152 | A | 3/1988 | Wallsten et al. |
| 6,019,778 | A | 2/2000 | Wilson et al. |
| 2007/0191925 | A1* | 8/2007 | Dorn ................. A61F 2/95 623/1.12 |
| 2008/0082159 | A1 | 4/2008 | Tsenf et al. |
| 2010/0137967 | A1* | 6/2010 | Atlani ................. A61F 2/95 623/1.11 |
| 2010/0286756 | A1* | 11/2010 | Dorn ............... A61M 25/0108 623/1.11 |
| 2013/0018451 | A1* | 1/2013 | Grabowski ........... A61F 2/966 623/1.12 |

(Continued)

FOREIGN PATENT DOCUMENTS

| CN | 102469275 D | 5/2012 |
| DE | 102006004123 A1 | 8/2007 |

(Continued)

OTHER PUBLICATIONS

International Search Report and Written Opinion for International Application No. PCT/IB2018/01133, dated Jan. 28, 2019.

(Continued)

*Primary Examiner* — George J Ulsh
(74) *Attorney, Agent, or Firm* — Arent Fox LLP

(57) ABSTRACT

Various embodiments for a stent delivery device that utilizes a wheel for slow retraction of an outer sheath and a slider for fast retraction of the outer sheath during delivery of a self-expanding implantable device such as a stent or stent graft.

17 Claims, 7 Drawing Sheets

(56) References Cited

U.S. PATENT DOCUMENTS

2013/0297011 A1* 11/2013 Morris .................. A61F 2/2436
                                                        623/2.11
2018/0280173 A1* 10/2018 Jimenez, Jr. ............ A61F 2/966

FOREIGN PATENT DOCUMENTS

| JP | 2007512061 A | 5/2007 |
|---|---|---|
| WO | 2005/053574 A2 | 6/2005 |

OTHER PUBLICATIONS

International Preliminary Report on Patentability in International Patent Application No. PCT/IB2018/001133, dated Mar. 17, 2020.
Notice of Reasons for Rejection in corresponding Japanese Patent Application No. 2019-565393, dated Jan. 5, 2021.
Office Action from corresponding Chinese Patent Application No. 201880036043.1, dated Apr. 2, 2021.

* cited by examiner

STENT DELIVERY CATHETER WITH FAST SLIDER AND SLOW THUMBWHEEL CONTROL

PRIORITY CLAIM AND RELATED APPLICATIONS

This application claims priority under 35 U.S.C. § 119 or the Paris Convention from U.S. Provisional Patent Application 62/557,923 filed Sep. 13, 2017, the entire contents of which is incorporated herein by reference as if set forth in full herein.

BACKGROUND

It is well known to employ various intravascular endoprostheses delivered percutaneously for the treatment of diseases of various body vessels. These types of endoprosthesis are commonly referred to as "stents". A stent (which includes covered stents or stent-graft) is a generally longitudinal tubular device of biocompatible material, such as stainless steel, cobalt-chromium, nitinol or biodegradable materials, having holes or slots cut therein to define a flexible framework so they can be radially expanded, by a balloon catheter or the like, or alternately self-expanded due to its shape memory characteristic of the material within a biological vessel. The stents are usually configured as a series of hoops with each defined by cylinder-like framework. The framework is usually a series of alternating sequence of struts with a vertex between each pair of struts and configured so that the vertex of one hoop facing a vertex of the adjacent hoops may be connected together. The struts are configured to move and thereby allow the stent to be compressed or "crimped" into a smaller outer diameter so that they can be mounted inside a delivery system.

The delivery systems are used to convey the stent to a desired location for treatment, and then deploy them in position. Many such stents are resiliently compressed to a smaller initial size for containment, protection, storage and eventual delivery from inside a catheter system. Upon deployment, the stents may resiliently self-expand to a larger deployed size.

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10 of Wilson, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al., on Mar. 22, 1988.

In operation, these known stent delivery systems are generally advanced within a body of a patient along a desired vascular path or other body passageway, until the stent within the catheter system is located at a desired site for treatment. While watching the relative positions of the stent and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a stent as the outer sheath is retracted. This gradual expansion presents an opportunity for a possible reverse "watermelon-seed" phenomenon to occur. This reverse watermelon-seed effect may cause the resilient stent to tend to push the outer sheath back in a proximal direction with a force that tends to change as the sheath is progressively retracted.

As a result, the physician may need to accurately hold the two proximal hubs in a specific relative position, holding them against this expansion force, while attempting to very accurately position the stent up until contact with the anatomy. One of the possibilities that may affect the positioning of the deployed stent is that the inner shaft should preferably be held stationary in the desired position. If the physician's hand that holds the inner shaft hub does inadvertently move during deployment, it is possible that the stent may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the stent may be adjusted up until the point at which a portion of the expanding portion of the stent touches the sidewalls of the body passage, so that the position of the stent should preferably be carefully adjusted until immediately before a portion of the stent touches the anatomy.

Some known catheter systems require two-handed operation, such as those with a pair of independent hubs, one hub on the inner and outer shaft member, respectively. Other known catheter systems include a pistol and trigger grip, with a single mode of deployment, involving a single trigger pull to deploy the associated stent.

SUMMARY OF THE DISCLOSURE

Applicant has devised a stent delivery system that includes a catheter tip, housing, slider and a wheel. The catheter tip is coupled to an inner shaft and an outer sheath with a stent disposed between the inner shaft and the outer sheath. The inner shaft and the outer sheath extends from a distal end to a proximal end. The housing extends along a longitudinal axis from a first end to a second end and defining a slot that extends for a portion of the longitudinal axis. The slider is disposed in the slot and coupled to the outer sheath so that movement of the slider results in movement of the outer sheath relative to the inner shaft. The wheel is mounted on the housing and coupled to the slider by a flexible member such that rotation of the wheel causes the outer sheath to move along the longitudinal axis.

A method of delivering a self-expanding stent to selected location in a body vessel can be achieved by: moving a stent to a selected location, the stent being disposed adjacent a catheter tip and confined between an inner shaft and an outer sheath at a distal end of a delivery system; winding a flexible member connected to the outer sheath so that the outer sheath is moved relative to the inner shaft along a direction from the distal end toward a proximal end of the delivery system to allow a portion of the self-expanding stent to be expanded into the body vessel; and translating a slider member coupled to the outer sheath to move the outer sheath relative to the inner shaft along a direction from the distal end toward a proximal end of the delivery system.

For each of the embodiments described above, the following features can be utilized in various permutations with each of the embodiments. For example, the flexible member comprises a belt configured to be wound about a rotational axis defined by the wheel; the flexible member comprises a wire configured to be wound about a rotational axis defined by the wheel; the outer sheath is coupled to the slider by a flexible member and the flexible member is configured to be wound about a rotational axis defined by the wheel; the wheel is mounted offset with respect to the longitudinal axis; the wheel is mounted orthogonal with respect to the longitudinal axis; the outer sheath is coupled to the slider by a mechanical link; the slider comprises a pulley member and the outer sheath is coupled to the slider by engaging the pulley member with the flexible member; or rotation of the wheel is configured to cause less translation of the outer sheath as compared to actuation of the slider for a given amount of movement.

These and other embodiments, features and advantages will become apparent to those skilled in the art when taken with reference to the following more detailed description of the exemplary embodiments of the invention in conjunction with the accompanying drawings that are first briefly described. As well, it is intended that these embodiments, features and advantages may be claimed in this or additional applications for patents.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "stent" is intended to encompass an uncovered framework as well as one that is covered by a suitable material (e.g., stent-graft). The term "proximal" is used to denote the location closer to the operator and "distal" is used to denote a location further away from the operator or the health care provider.

Figure 1:
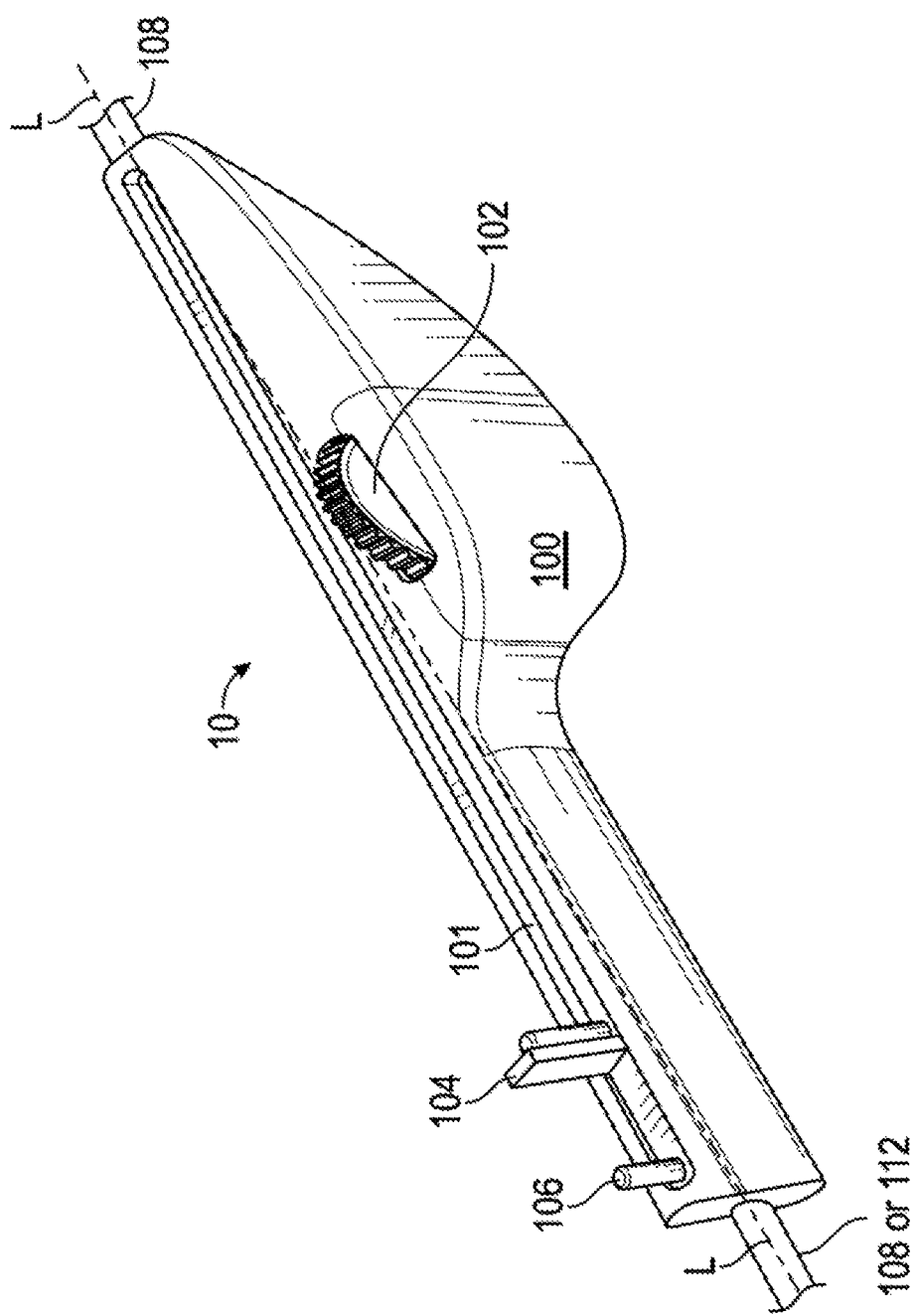
FIG. 1 illustrates a perspective view of a handle according to an embodiment.

Referring now to the figures wherein like numerals indicate the same element throughout the views, a portion of the delivery system 10 in the form of a handle that defines a housing 100 is shown in FIG. 1. The housing 100 extends along a longitudinal axis L-L from a proximal end to a distal end. The housing 100 provides a slot 101 that extends along a portion of the longitudinal axis L-L. An outer sheath 108 is configured for movement along the longitudinal axis L-L. Two modes are provided for causing relative translational movement of outer sheath 108 along axis L-L, either through actuation of slider 104, which is disposed in the slot 101 or rotation of wheel 102, which is mounted on the housing 100. Outer sheath 108 may be coupled to slider 104 and wheel 102 in various configurations depending on the embodiment to achieve relatively coarse control over outer sheath movement 108 through slider 104 and relatively fine control over outer sheath movement 108 through wheel 102 as described in further detail below.

Figure 2:
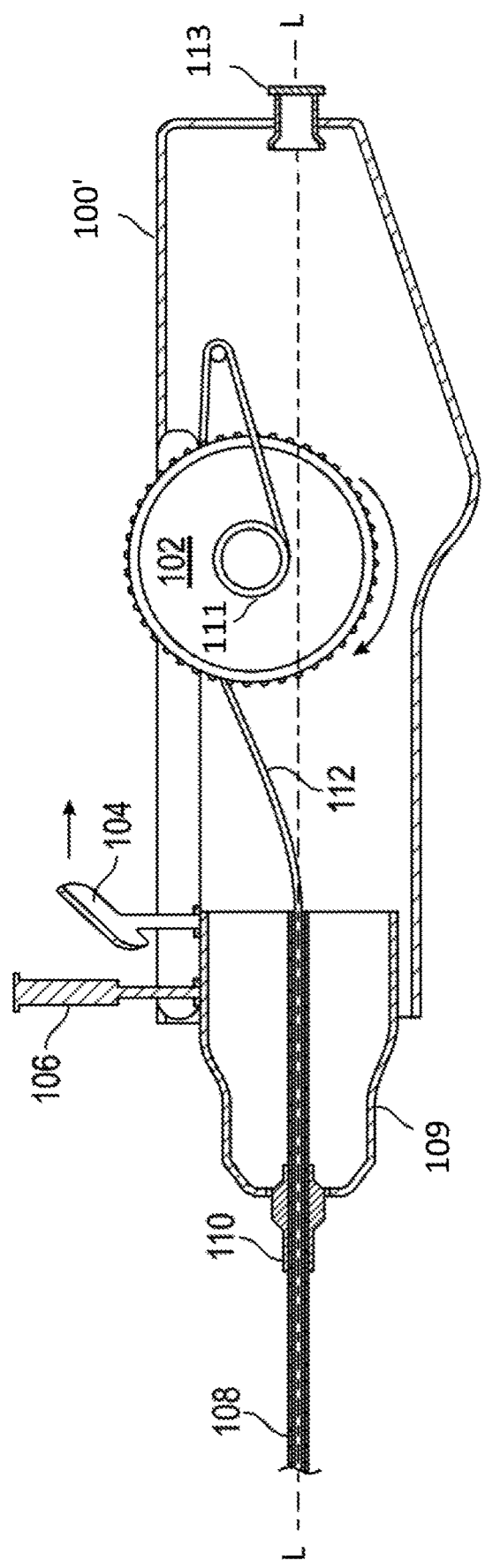
FIG. 2 illustrates a sectioned side view of an embodiment of the handle in FIG. 1.

For example, in the embodiment is shown in FIG. 2, slider 104 is mechanically connected to link 109, which is in turn connected to outer sheath 108. As will be appreciated, actuation of slider 104 by translating it longitudinally along slot 101 (not shown in FIG. 2) causes a corresponding longitudinal translation of outer sheath 108 in the proximal direction, due to the coupling provided by link 109. Additionally, outer sheath 108 is also coupled to flexible member 112, which is configured to be wound about axle 111 of wheel 102. Correspondingly, rotation of wheel 102 winds flexible member 112 around axle 111 and results in proximal translation of outer sheath 108 along axis L-L. In this embodiment, rotation of wheel 102 causes longitudinal movement of slider 104 as well as outer sheath 108. Further, the movement of slider 104 is directly translated to movement of outer sheath 108, so that motion of slider 104 causes outer sheath 108 to undergo the same degree of motion. On the other hand, depending on the relationship between the diameters of axle 111 and wheel 102, the ratio of rotational distance experienced by wheel 102 to the distance of translational movement caused in outer sheath 108 will vary. In general, relatively less movement is imparted to outer sheath 108 so long as the diameter of axle 111 is less than the diameter of wheel 102. Correspondingly, the use of these components and this configuration allows fine adjustment to pull the outer sheath 108 back slightly when employing wheel 102 and coarse adjustment when employing slider 104.

Thus, the different mechanical advantages associated with these two modes facilitate moving outer sheath 108 at a first rate of movement (using wheel 102) that allows for precise exposure and initial deployment of the medical device and at a second, greater rate of movement (using slider 104) to complete deployment of the medical device more quickly once the physician is satisfied with its placement. In other words, a given amount of movement of wheel 102 (rotational) causes less translation of outer sheath 108 than the same amount of movement of slider 104 (longitudinal translation). Since relatively less motion of slider 104 is needed, the physician may correspondingly withdraw outer sheath 108 more quickly when desired by employing slider 104 as opposed to wheel 102.

For purposes of flushing or insertion of a guidewire or other accessories into the body vessel 300, a distal luer port 106 and/or a proximal luer port 113 may be provided at respective ends of the housing 100. For example, distal luer port 106 allows flushing between outer sheath 108 and an inner shaft (such as inner shaft 80, FIG. 6), while proximal luer port 113 allows flushing the inside of a guidewire tube (not shown). Depending on the configuration, the ports may be coupled to the outer sheath 108 by a suitable coupling including a slip coupling to allow the outer sheath 108 to slide over a smaller tubular member (not shown) of the luer ports.

Figure 3:
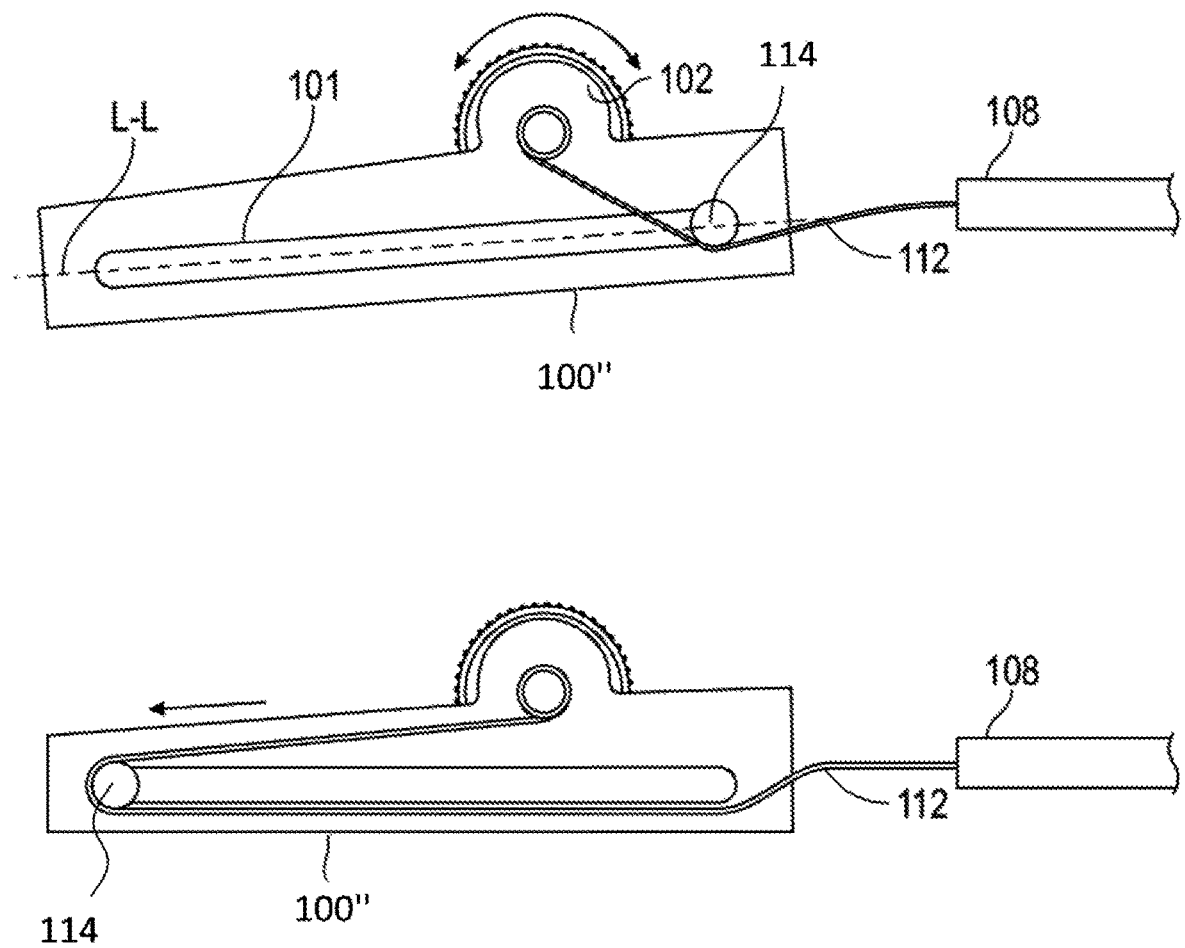
FIG. 3 illustrates a plan view of another embodiment of the handle in FIG. 1.

As another example, the schematic embodiment shown in FIG. 3 features a coupling between the outer sheath 108 and the slider 104 by a flexible member 112, which is again configured to be wound about a rotational axis defined by the wheel 102. Depending on the configuration, flexible member 112 may extend from housing 100" and be attached to outer sheath 108 at a distal location or may be attached within the housing. In this embodiment, flexible member 112 is engaged by pulley member 114 of slider 104. Again, this configuration achieves relatively coarse control over outer sheath movement 108 through slider 104 and relatively fine control over outer sheath movement 108 through wheel 102. In particular, rotation of wheel 102 as indicated in the top view winds flexible member 112 around axle 111 and results in proximal translation of outer sheath 108 along axis L-L in a similar manner to that described above. Actuation of slider 104 by translating it longitudinally along slot 101 as indicated in the bottom view causes pulley member 114 to move proximally within housing 100". Wheel 102 does not rotate during actuation of slider 104, so the movement of pulley member 114 causes a corresponding longitudinal translation of outer sheath 108 in the proximal direction. To achieve this result, wheel 102 may be configured to rotate in only one direction, may have a locking mechanism, may be restrained by the physician or other implementations may be used as warranted. As with the embodiment in FIG. 2, the movement of slider 104 is directly translated to movement of outer sheath 108, causing outer sheath 108 to undergo the same degree of motion and relatively less movement is imparted to outer sheath 108 by sizing the diameter of axle 111 to be less than the diameter of wheel 102. Once more, this configuration allows fine adjustment to pull the outer sheath 108 back slightly when employing wheel 102 and coarse adjustment when employing slider 104. Thus, the different mechanical advantages associated with these two modes facilitate moving outer sheath 108 at a first rate of movement (using wheel 102) that allows for precise exposure and initial deployment of the medical device and at a second, greater rate of movement (using slider 104) to complete deployment of the medical device more quickly once the physician is satisfied with its placement.

Figure 4A:
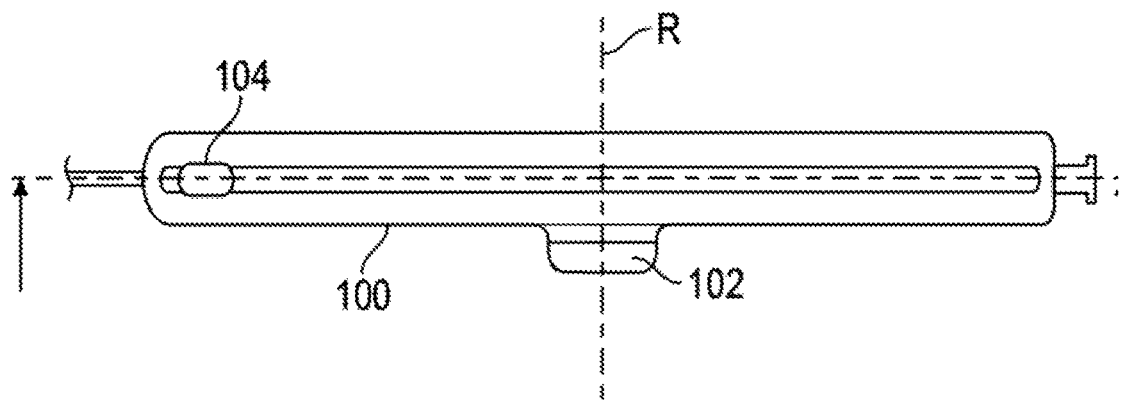
FIGS. 4A and 4B illustrate yet another embodiment of the handle in FIG. 1 with the principles of FIGS. 1-3.
Figure 4B:
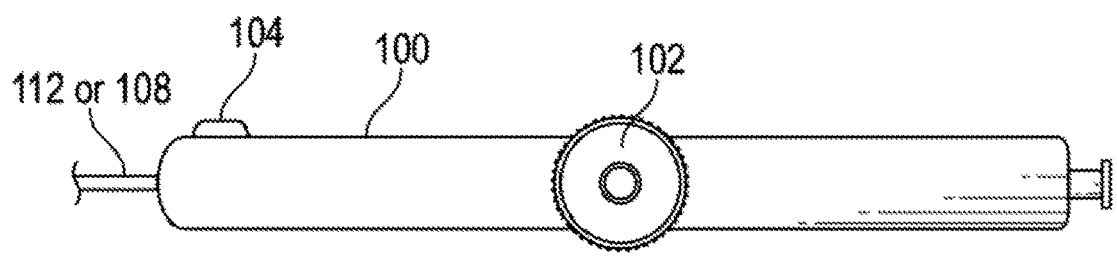
Figure 4C:
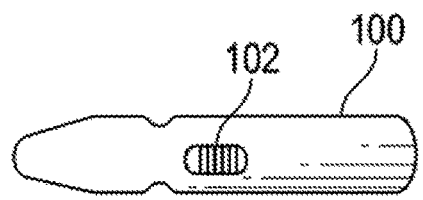
FIGS. 4C-4F illustrate additional embodiments of the handle with the principles of FIGS. 1-3.
Figure 4D:
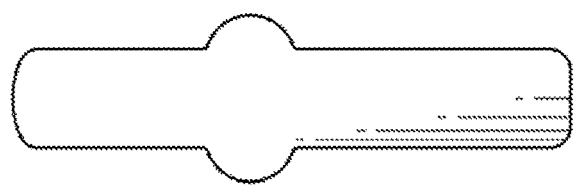
Figure 4E:
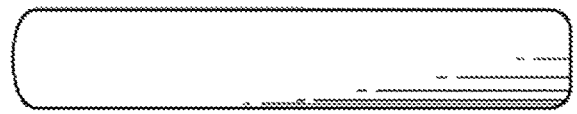
Figure 4F:
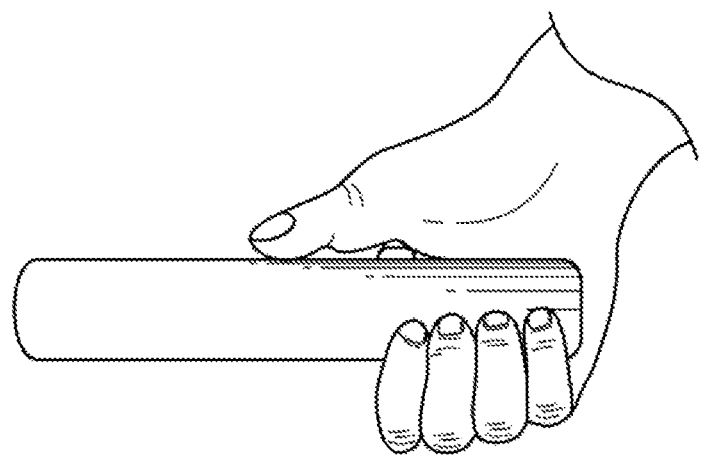

In either of these embodiments or others, the wheel is mounted offset with respect to the longitudinal axis L-L as shown in FIGS. 4A and 4B. Alternatively, the wheel can be mounted in line with respect to the longitudinal axis such that the wheel is surrounded on either side by the housing 100 as shown here in FIG. 4C. Similarly, the flexible member 112 may be in the form of a belt configured to be wound about a rotational axis R defined by the wheel 102 (FIG. 4A). Alternatively, the flexible member 112 may be in the form of a wire configured to be wound about the rotational axis R defined by the wheel 102.

Figure 5:
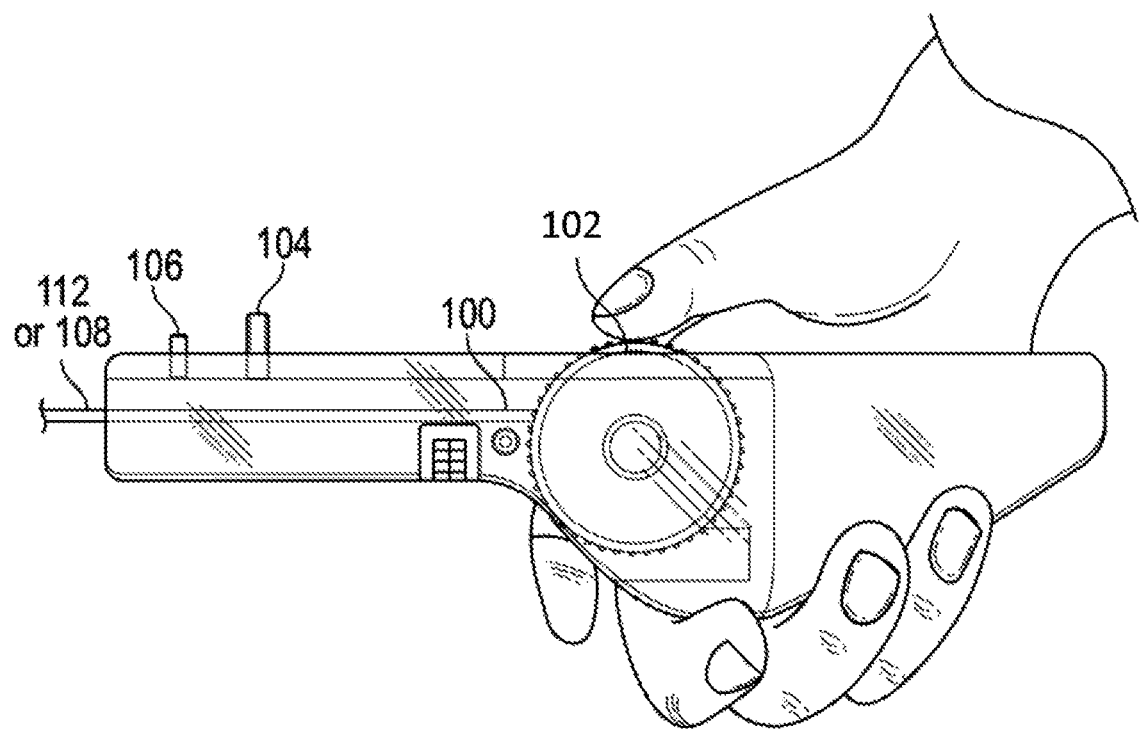
FIG. 5 is a photograph of a prototype of the embodiment of FIG. 1.

FIG. 5 shows another exemplary embodiment including similar components discussed in FIGS. 1-3 earlier.

Figure 6A:
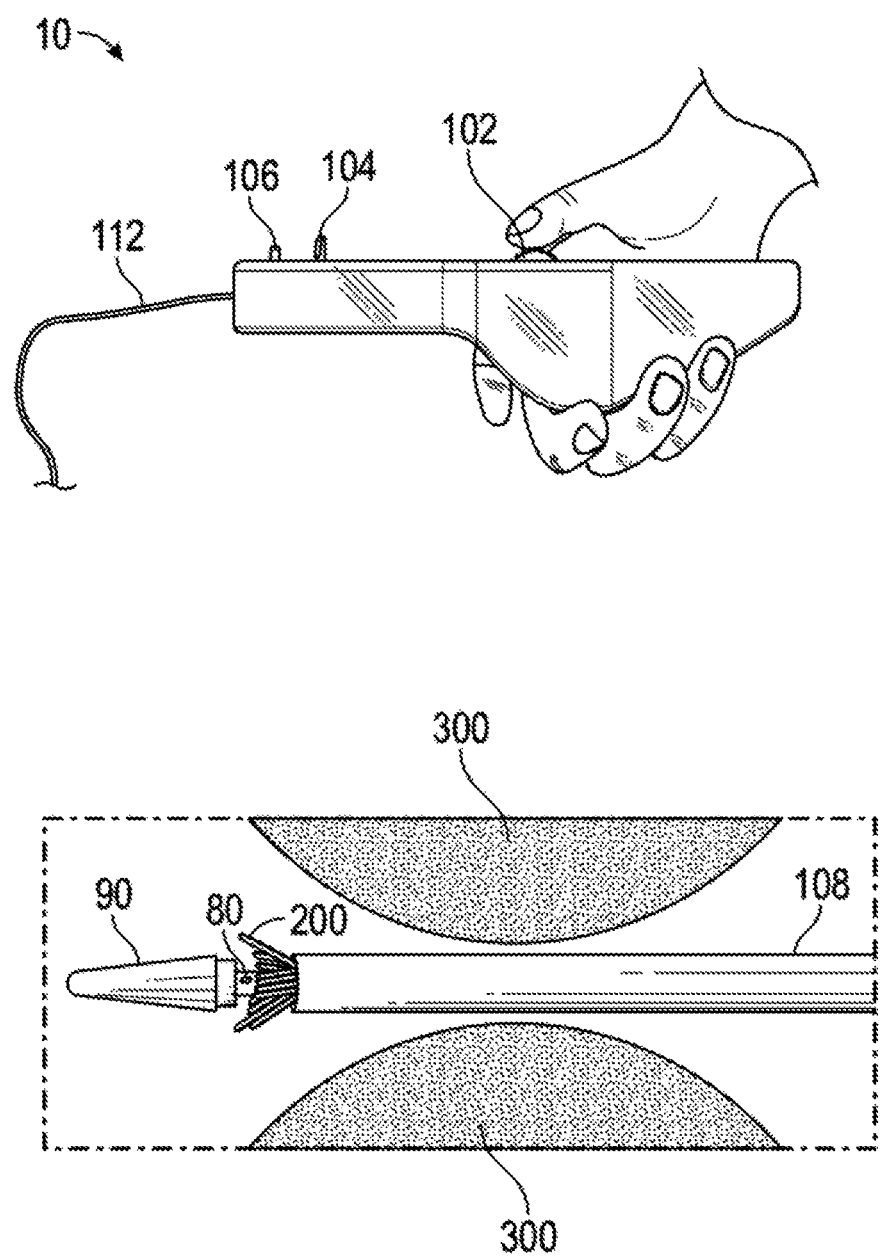
FIGS. 6A and 6B illustrate the operation of the system.
Figure 6B:
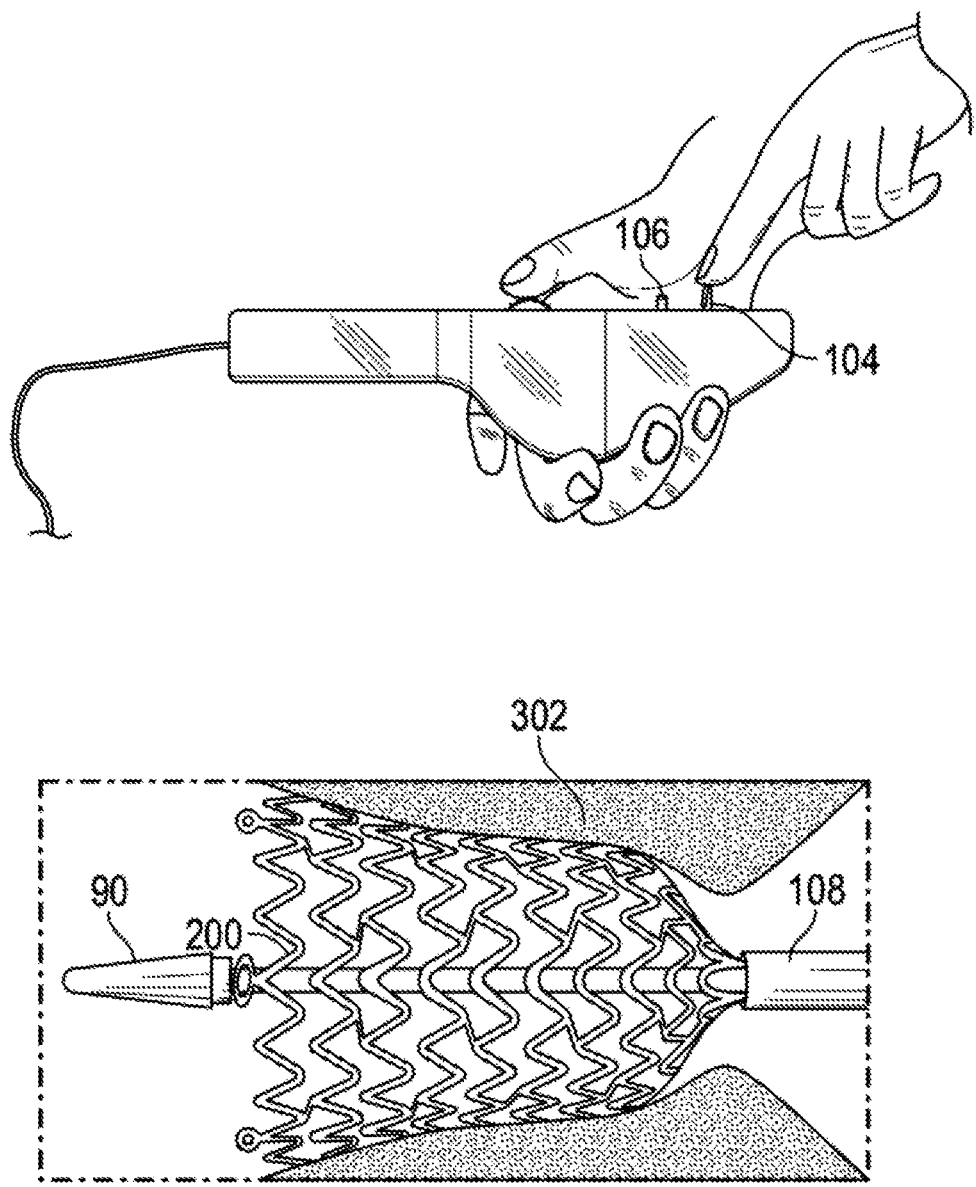

In operation, the distal end of the medical device delivery system 10 is preferably directed into a patient via a body passageway 300. The medical device delivery system 10 may preferably follow along a guidewire (not shown) or travel through a previously placed guiding catheter (not shown), until the distal tip 90 is at a desired location in the body vessel 300 for treatment. As shown in FIG. 6B, the distal tip 90 has preferably crossed the site of a lesion or stenosis 302. When the device is properly in an initial position (FIG. 6A), the physician releases or breaks off the lock of the handle (not shown for brevity and not required in all embodiments). The lock may be releasable only once, or may be capable of repeatedly being engaged and released. Such a locking mechanism preferably resists inadvertent or accidental movement or retraction of the stent delivery system components during packaging, sterilization, shipping, storage, handling and preparation.

After the lock is released, the wheel 102 can be rotated slowly such that the outer sheath 108 is retracted towards the operator. In a first mode, the use of the wheel 102 coupled to the outer sheath 108 allows precise and sensitive adjustment to pull the outer sheath 108 back slightly. This small movement exposes a small portion of the medical device, in this case a stent 200, as shown in FIG. 6A. In this configuration, the handle 100 will hold the outer sheath 108 in position relative to the inner shaft 80, resisting further inadvertent expansion of the stent 200. The physician then has the time and flexibility of procedure to selectively optimize and make any final adjustments to the position of the medical device and delivery system within the desired site, as illustrated in FIG. 6A. This precise adjustment of the position of the stent 200, before any portion of the stent 200 touches the body passage or vessel 300 in a manner that might inhibit further positional adjustment, is preferable.

When the physician is satisfied with the positioning, as it appears on a fluoroscopic x-ray video screen for example, the physician may continue to rotate the wheel 102 to further withdraw the outer sheath 108, as shown in FIG. 6A. Rotation of the wheel 102 may be performed with the same hand holding housing 100.

Upon initial contact of the stent 200 with the vessel wall, or when the stent is 200 expanded sufficiently to independently hold its position, or at any desired point, the physician may simply grasp slider 104 and pull or push it along slot 101, as shown in FIG. 6B. This second mode of withdrawing the outer sheath 108 allows relatively large-scale and rapid movement, at whatever speed the physician wishes, to quickly deploy the medical device. The physician may hold housing 100 in one hand and actuate the slider 104 with the other hand.

Various materials may be selected for the components of the present invention, including any material having the desirable performance characteristics. In the particular embodiment shown in the drawings, the inner and outer shaft members and, strain relief and distal tip may be made of any biocompatible and suitably flexible yet sufficiently strong material, including polymers of various types. Possible selections for such materials include nylons or polyamides, polyimides, polyethylenes, polyurethanes, polyethers, polyesters, etc. In the alternative, some portion or all of the inner and/or outer shaft member may be formed of a flexible metal, including for example stainless steel or nitinol hypotube. The stem 200 is preferably made of any biocompatible material that is strong and rigid, including for example stainless steel, platinum, tungsten, etc. The components of the handle of the present invention are preferably made of a material that is strong and rigid, including for example inflexible polycarbonates, or even some metal components. In addition, the inner shaft member distal tip may preferably be provided with a through lumen adapted to receive a guidewire.

Of course, many different variations are included within the scope of the present invention. Some of these variations or alternative embodiments include any possible arrangement of sizes, materials, and designs within the scope of the claims.

By virtue of the disclosure provided herein, a method of delivering a self-expanding stent to selected location in a body vessel 300 can be utilized. The method can be achieved by: moving a stent 200 to a selected location, the stent being disposed adjacent a catheter tip 90 and confined between an inner shaft 80 and an outer sheath 108 at a distal end of a delivery system 10; winding a flexible member 112 connected to the outer sheath 108 so that the outer sheath is moved relative to the inner shaft 80 along a direction from the distal end toward a proximal end of the delivery system to allow a portion of the self-expanding stent 200 to be expanded into the body vessel 300; and translating a slider member 104 coupled to the outer sheath 108 to move the outer sheath relative to the inner shaft along a direction from the distal end toward a proximal end of the delivery system. The outer sheath 108 may undergo relatively less translation along the longitudinal axis due to rotation of the wheel 102 as compared to actuation of the slider 104 for a given amount of movement. The outer sheath may be translated at a first rate by rotating the wheel and at a second rate by actuating the slider, wherein the second rate is relatively greater than the first rate.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A stent delivery system comprising:
   a catheter tip coupled to an inner shaft and an outer sheath with a stent disposed between the inner shaft and the outer sheath, the inner shaft and the outer sheath extending from a distal end to a proximal end;
   a housing extending along a longitudinal axis from a first end to a second end, the housing defining a slot extending for a portion of the longitudinal axis;
   a slider disposed in the slot and coupled to the outer sheath by a flexible member so that movement of the slider transmits force through the flexible member to cause movement of the outer sheath relative to the inner shaft; and
   a wheel mounted on the housing and coupled to the slider by the flexible member such that rotation of the wheel causes the outer sheath to move along the longitudinal axis, wherein rotation of the wheel is configured to cause less translation of the outer sheath as compared to actuation of the slider for a given amount of movement and wherein the slider and the wheel are configured to move relative to each other.

2. The stent delivery system of claim 1, in which the outer sheath is coupled to the slider by the flexible member and the flexible member is configured to be wound about a rotational axis defined by the wheel.

3. The stent delivery system of claim 1, in which the wheel is mounted offset with respect to the longitudinal axis.

4. The stent delivery system of claim 1, in which the wheel is mounted aligned with respect to the longitudinal axis.

5. The stent delivery system of claim 1, in which rotation of the wheel causes the slider as well as the outer sheath to move along the longitudinal axis.

6. The stent delivery system of claim 1, in which the outer sheath is coupled to the slider by a mechanical link.

7. The stent delivery system of claim 1, wherein the slider comprises a pulley member and in which the outer sheath is coupled to the slider by engaging the pulley member with the flexible member.

8. A stent delivery system comprising:
   a housing extending along a longitudinal axis from a proximal end to a distal end, the housing defining a slot extending along a portion of the longitudinal axis;
   an outer sheath configured for movement along the longitudinal axis, the outer sheath being coupled by a flexible member to a slider disposed in the slot, so that movement of the slider transmits force through the flexible member to cause movement of the outer sheath; and
   a wheel mounted on the housing and coupled to the outer sheath by the flexible member such that rotation of the wheel causes the outer sheath to move along the longitudinal axis, wherein rotation of the wheel is configured to cause less translation of the outer sheath as compared to actuation of the slider for a given amount of movement and wherein the slider and wherein the slider and the wheel are configured to move relative to each other.

9. The stent delivery system of claim 8, in which the flexible member is configured to be wound about a rotational axis defined by the wheel.

10. The stent delivery system of claim 8, in which the wheel is mounted offset with respect to the longitudinal axis.

11. The stent delivery system of claim 8, in which the wheel is mounted aligned with respect to the longitudinal axis.

12. The stent delivery system of claim 8, in which rotation of the wheel causes the slider as well as the outer sheath to move along the longitudinal axis.

13. The stent delivery system of claim 8, in which the outer sheath is coupled to the slider by a mechanical link.

14. The stent delivery system of claim 8, wherein the slider comprises a pulley member and in which the outer sheath is coupled to the slider by engaging the pulley member with the flexible member.

15. A method of delivering a self-expanding stent to selected location in a body vessel, the method comprising:
  moving a stent to a selected location, the stent being disposed adjacent a catheter tip and confined between an inner shaft and an outer sheath at a distal end of a delivery system;
  winding a flexible member connected to the outer sheath so that the outer sheath is moved relative to the inner shaft along a direction from the distal end toward a proximal end of the delivery system to allow a portion of the self-expanding stent to be expanded into the body vessel;
  rotating a wheel coupled to the outer sheath by the flexible member to move the outer sheath relative to the inner shaft along a direction from the distal end toward a proximal end of the delivery system; and
  translating a slider member coupled to the outer sheath by the flexible member to move the outer sheath relative to the inner shaft along a direction from the distal end toward a proximal end of the delivery system,
  wherein rotation of the wheel is configured to cause less translation of the outer sheath as compared to actuation of the slider for a given amount of movement and wherein the slider and wherein the wheel and the slider are configured to move relative to each other.

16. The method of claim 15, wherein the outer sheath undergoes relatively less translation along the longitudinal axis due to rotation of the wheel as compared to actuation of the slider for a given amount of movement.

17. The method of claim 16, further comprising translating the outer sheath at a first rate by rotating the wheel and translating the outer sheath at a second rate.

\* \* \* \* \*